United States Patent
Jago et al.

(10) Patent No.: US 10,368,844 B2
(45) Date of Patent: Aug. 6, 2019

(54) AUTOMATED BIPLANE-PW WORKFLOW FOR ULTRASONIC STENOSIS ASSESSMENT

(71) Applicant: KONINKLIJKE PHILIPS N.V., Eindhoven (NL)

(72) Inventors: James Robertson Jago, Eindhoven (NL); Keith William Johnson, Eindhoven (NL); Ashraf Saad, Eindhoven (NL); David Allen Hull, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 855 days.

(21) Appl. No.: 14/431,463

(22) PCT Filed: Sep. 27, 2013

(86) PCT No.: PCT/IB2013/058915
§ 371 (c)(1),
(2) Date: Mar. 26, 2015

(87) PCT Pub. No.: WO2014/049558
PCT Pub. Date: Apr. 3, 2014

(65) Prior Publication Data
US 2015/0250453 A1 Sep. 10, 2015

Related U.S. Application Data

(60) Provisional application No. 61/706,165, filed on Sep. 27, 2012.

(51) Int. Cl.
*A61B 8/08* (2006.01)
*A61B 5/02* (2006.01)
(Continued)

(52) U.S. Cl.
CPC .............. *A61B 8/488* (2013.01); *A61B 5/02* (2013.01); *A61B 8/06* (2013.01); *A61B 8/145* (2013.01);
(Continued)

(58) Field of Classification Search
CPC ........... A61B 8/488; A61B 8/483; A61B 8/06; A61B 8/5223; A61B 8/145; A61B 5/02;
(Continued)

(56) References Cited

U.S. PATENT DOCUMENTS 5,769,079 A 6/1998 Hossack
6,086,539 A 7/2000 Guracar et al.
(Continued)

FOREIGN PATENT DOCUMENTS

EP 1152364 A2 7/2011
JP 2008073422 A 4/2008
(Continued)

OTHER PUBLICATIONS

"New Direction of Biplane Transesophageal Echocardiography With Special Emphasis on Real-Time Biplane Imaging and Matrix Phased-Array Biplane Transducer" Omoto et al, Echocardiography, vol. 7, No. 6, Nov. 1, 1990 p. 691-698.
(Continued)

*Primary Examiner* — Amanda Lauritzen Moher

(57) ABSTRACT

An ultrasound system with a matrix array (500) probe (10) operable in the biplane mode is used to assess stenosis of a blood vessel by simultaneously displaying two color Doppler biplane images (60a, 60b) of the vessel, one a longitudinal cross-sectional view (60a) and the other a transverse cross-sectional view (60b). The two image planes intersect along a Doppler beam line (68) used for PW Doppler. A sample volume graphic (SV) is positioned over the blood vessel at the peak velocity location in one image, then
(Continued)

positioned over the blood vessel at the peak velocity location in the other image. As the sample volume location is moved in one image, the plane and/or sample volume location of the other image is adjusted correspondingly. Spectral Doppler data (62) is then acquired and displayed from the sample volume location.

14 Claims, 6 Drawing Sheets

(51) Int. Cl.
*G06T 7/00* (2017.01)
*G01S 15/89* (2006.01)
*A61B 8/06* (2006.01)
*A61B 8/14* (2006.01)
*G01S 7/52* (2006.01)

(52) U.S. Cl.
CPC ............ *A61B 8/483* (2013.01); *A61B 8/5223* (2013.01); *G01S 7/52063* (2013.01); *G01S 7/52066* (2013.01); *G01S 7/52073* (2013.01); *G01S 7/52074* (2013.01); *G01S 15/8915* (2013.01); *G01S 15/8925* (2013.01); *G01S 15/8979* (2013.01); *G01S 15/8988* (2013.01); *G01S 15/8993* (2013.01); *G06T 7/0012* (2013.01); *G01S 7/5208* (2013.01)

(58) Field of Classification Search
CPC ............ G01S 15/8915; G01S 15/8979; G01S 15/8993; G01S 7/52063; G01S 7/52066; G01S 15/8925; G01S 7/52073; G01S 7/52074; G01S 7/5208; G01S 15/8988; G06T 7/0012
See application file for complete search history.

(56) References Cited

U.S. PATENT DOCUMENTS

| | | | |
|---|---|---|---|
| 6,322,509 B1 | 11/2001 | Pan et al. | |
| 6,709,394 B2 | 3/2004 | Frisa et al. | |
| 2001/0016686 A1* | 8/2001 | Okada | A61B 8/06 600/454 |
| 2003/0073907 A1* | 4/2003 | Taylor | A61B 8/12 600/459 |
| 2005/0124885 A1* | 6/2005 | Abend | A61B 8/06 600/443 |
| 2005/0281444 A1* | 12/2005 | Lundberg | A61B 8/08 382/128 |
| 2008/0039725 A1 | 2/2008 | Man et al. | |
| 2008/0051661 A1* | 2/2008 | Kataguchi | A61B 5/0402 600/455 |
| 2008/0242996 A1 | 10/2008 | Hall et al. | |
| 2011/0319766 A1* | 12/2011 | Tsuruno | A61B 8/04 600/454 |
| 2012/0078106 A1* | 3/2012 | Dentinger | A61B 8/06 600/454 |
| 2013/0165785 A1* | 6/2013 | Lause | A61B 8/06 600/443 |
| 2014/0221838 A1 | 8/2014 | Loupas | |

FOREIGN PATENT DOCUMENTS

| | | |
|---|---|---|
| WO | 1996017549 | 6/1996 |
| WO | 2003019227 | 3/2003 |

OTHER PUBLICATIONS

"Evaluation of Biplane Color Doppler Transesophageal Echocardiolgraphy in 200 Consecutive Patients" Omoto et al, Circulation, vol. 85, No. 4, Apr. 1, 1992, p. 1237-1247.

"Biplane Transesopageal Echocardiography . . . " Wang et al, American Heart Journal, vol. 123, No. 4, Apr. 1, 1992. p. 1027-1038.

* cited by examiner

AUTOMATED BIPLANE-PW WORKFLOW FOR ULTRASONIC STENOSIS ASSESSMENT

This application is the U.S. National Phase application under 35 U.S.C. § 371 of International Application No. PCT/IB2013/058915, filed on Sep. 27, 2013, which claims the benefit of U.S. Provisional Application No. 61/706,165 filed on Sep. 27, 2012. These applications are hereby incorporated by reference herein.

This invention relates to medical diagnostic systems and, in particular, to diagnostic ultrasound systems for assessing blood flow through stenotic blood vessels or at other points in the cardiovascular system.

A significant procedure in many standard vascular ultrasound exams is to obtain an assessment of a stenosis, or narrowing, of an artery. This is typically assessed using Color Doppler to find the stenosis and PW-Doppler to measure the peak flow velocity, which is correlated with the degree of stenosis. Although this is a well established workflow for assessing a vascular stenosis, it is subject to a number of limitations well known to clinical users. First, there are many manual steps involved that require an experienced user in order to perform them successfully and also can require a significant amount of time. Also, since the user can only visualize the vessel flow by means of the color Doppler display in one two dimensional (2D) image plane, the procedure requires repositioning the ultrasound probe by manually tilting it to precisely visualize the location of peak velocity blood flow. It is difficult for the user to be sure that she is actually aligned with the peak velocity flow. Experienced users utilize the Doppler audio to blindly locate the highest stenotic site in the perpendicular plane of the image. This takes time and can also result in inaccurate peak velocity measurements when the alignment is not precise. Finally, it is also difficult to be sure that the angle correction, which attempts to set the optimal angle between the flow direction and the Doppler line (and is required to determine the actual flow velocity), is correct when the vessel is only seen in one plane. Inaccurate angle correction can lead to the possibility of incorrect peak velocity measurements, and inconsistent results between repeat measurements, different users and different labs. Accordingly it is desirable to provide an ultrasound workflow for a vascular procedure which overcomes these sources of error, inaccuracy, and procedural difficulty.

In accordance with the principles of the present invention a diagnostic ultrasound system and workflow are described in which two imaging planes at different orientations are acquired and displayed simultaneously. The two planes are intersecting image planes in the body which enable visualization of the stenosis or site under investigation and angle correction in one plane and independent Doppler sample volume (SV) placement in both planes. A semi-automated implementation is described in which the two image planes automatically adjust their relative orientation to maintain visualization of the sample volume in both planes. In an automated implementation optimization of a number of steps of the workflow are performed automatically.

Figure 1:
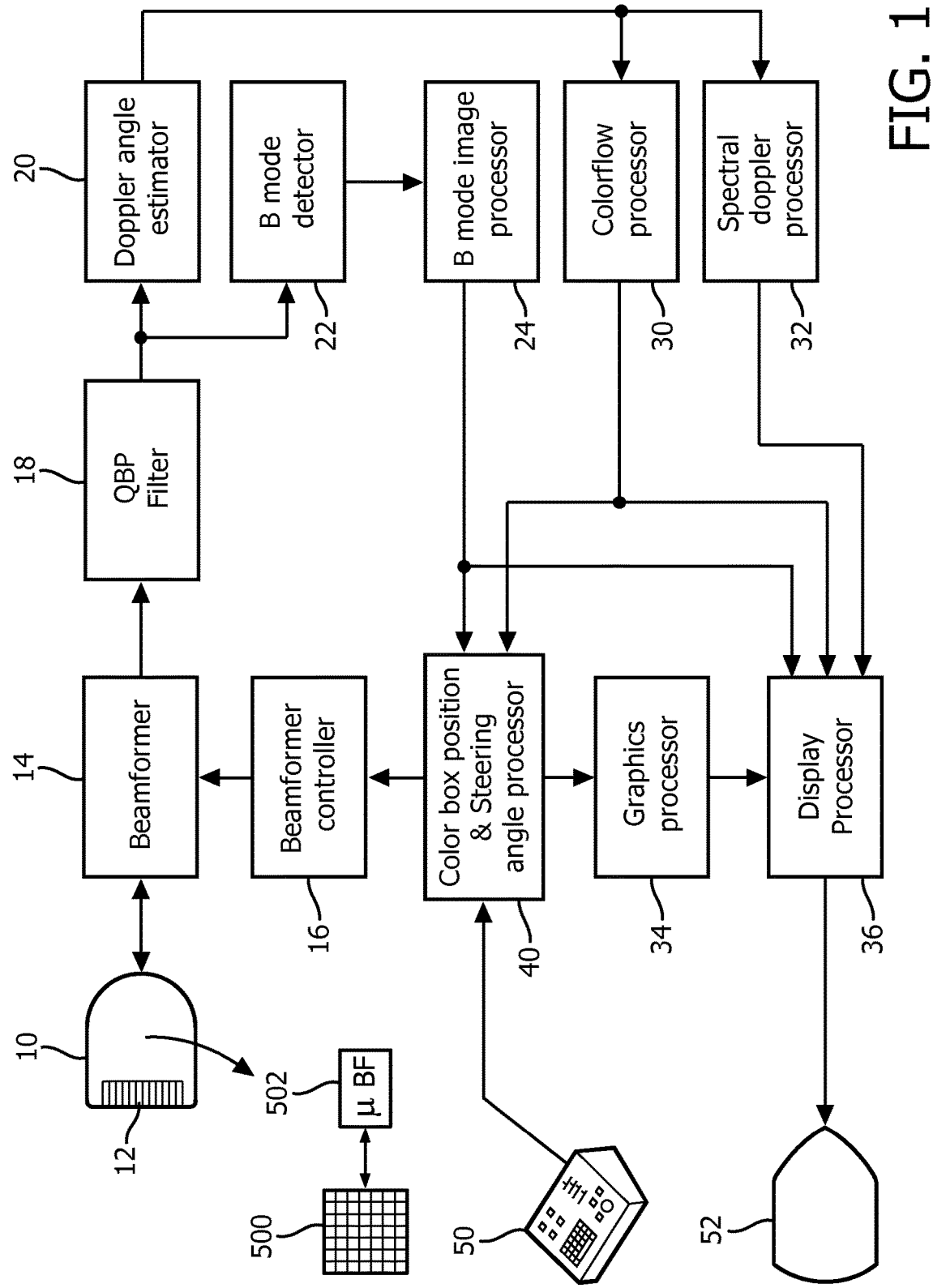
FIG. 1 illustrates in block diagram form an ultrasonic diagnostic imaging system constructed in accordance with the present invention.

Referring first to FIG. 1, an ultrasound system constructed in accordance with the principles of the present invention is shown in block diagram form. An ultrasound probe 10 contains a transducer array 12 of transducer elements which transmit ultrasound waves into the body and receive returning echo signals. The transmitted waves are directed in beams or scanlines to interrogate a region of interest in the body. A one-dimensional array can be used to transmit beams over a single plane for two dimensional imaging. For a stenosis assessment exam in accordance with the present invention, the probe 10 is a matrix array probe having a two-dimensional array of transducer elements 500 coupled to a probe microbeamformer 502. A matrix array probe can be used to transmit beams over a volumetric region of the body for three dimensional imaging. The beams can be steered and focused in different directions by the probe to interrogate tissue in specific locations or blood flow in specific directions as explained more fully below. For a workflow of the present invention the matrix array probe is operable in a biplane mode as described in U.S. Pat. No. 6,709,394 (Frisa et al.) in which two intersecting planes in a three dimensional region are scanned and imaged simultaneously. Control and processing of beams on transmit and receive is provided by a beamformer controller 16, which controls the microbeamformer 502 and a system beamformer 14 to transmit properly formed beams and beamform the received signals through delay and summation into coherent echo signals. In a two-stage beamforming system as shown in FIG. 1, partial beamforming of received signals is performed by the microbeamformer and completion of the beamforming process is performed by the system beamformer. The beamformers can control the transducer array to scan beams over a desired image plane, for example, and to repetitively scan beams over an area of the image plane in which blood flow is to be assessed at a pulse repetition frequency (PRF) appropriate for the velocities of blood flow present in that region of the body.

A quadrature bandpass filter 18 processes the echo signals into quadrature I and Q components. The separate components are used by a Doppler angle estimator 20 to estimate the phase or frequency shift of a Doppler signal at points where Doppler interrogation is to be performed. A B mode detector 22 uses the I and Q components to perform B mode detection for tissues images by taking the square root of the sum of the squares of the I and Q components. The detected echo intensities are processed by a B mode image processor 24 on a spatial basis to form a two or three dimensional image of the tissue in the body, which is processed for display by display processor 36 and displayed on display screen 52.

The Doppler frequencies at locations in the image plane which are produced by the Doppler angle estimator 20 can be mapped directly to velocity values of flow at those locations. This Doppler data is coupled to a colorflow processor 30 which spatially processes the data into a two or three dimensional image format, in which the velocity values are color-coded. This Doppler color map is overlaid over the spatially corresponding B mode image by the display processor 36 to illustrate the locations in the anatomy where flow is taking place and the velocity and direction of that flow by the color coding. Doppler data from a particular point in the image, selected by placement of a sample volume SV over that location in the image, is coupled to a spectral Doppler processor 32 which produces a spectral display of the variation and distribution of flow velocities at that point with time. The spectral Doppler display is forwarded to the display processor 36 for processing and display of the spectral Doppler display on the display screen 52.

For a stenosis exam workflow of the present invention, colorflow data from the colorflow processor 30 and, preferably, spatially corresponding B mode data from the B mode processor 24, is coupled to a color box position and steering angle processor 40. The color box position and steering angle processor controls the automation of settings and features of the colorflow image, including properly positioning the color box, setting the Doppler angle of the Doppler beams, locating the sample volume SV in the image, and proper positioning of the flow angle cursor for Doppler angle correction. For control of the Doppler angle the color box position and steering angle processor is coupled to the beamformer controller 16 to control the Doppler beam directions. Setup and control of the color box position and steering angle processor is provided by the setting of controls on a user control panel 50. Graphical display of functions controlled by the color box position and steering angle processor, such as the outline of the color box, the sample volume graphic, and the flow angle cursor, is provided through a graphics processor 34 which is coupled to the display processor 36 to overlay the graphics over the ultrasound images. The operation of the color box position and steering angle processor 40 is more fully described in U.S. patent application Ser. No. 61/541,353, entitled ULTRASOUND SYSTEM WITH AUTOMATED DOPPLER FLOW SETTINGS, and filed Sep. 30, 2011.

Figure 2:
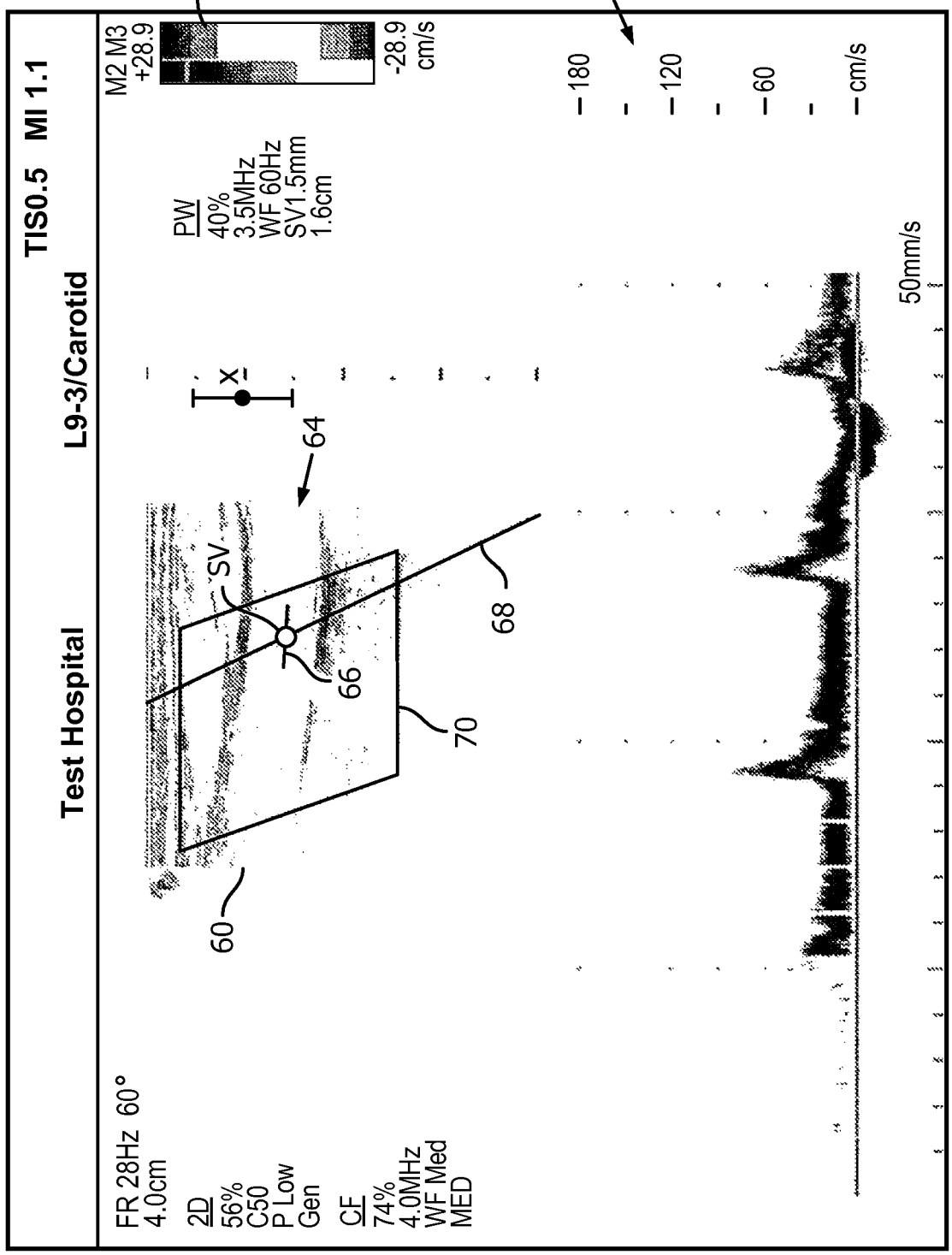
FIG. 2 illustrates an ultrasound display screen for a conventional ultrasound stenosis assessment exam.

FIG. 2 shows an ultrasound system display of a typical colorflow/spectral Doppler duplex image for conduct of a stenosis assessment exam in accordance with the current standard of practice. A two dimensional (2D) anatomical ultrasound image 60 is at the top of the screen and a spectral Doppler display 62 is at the bottom of the screen. Doppler interrogation is done inside the color box 70, and a colorflow image is displayed inside this box. The surrounding portion of the image outside the color box 70 is shown in B mode grayscale without the color Doppler overlay. The use of a color box delineates the region where Doppler is to be performed, and repeated Doppler transmission for Doppler ensemble acquisition is not performed outside of the color box. Restricting the Doppler transmission to only the color box eliminates the need for repeated line interrogation outside the box and hence limits the total number of transmit-receive cycles needed to produce the image, thereby reducing the time needed to acquire the image which improves the real time frame rate of display. The Doppler beams for the spectral Doppler data are transmitted and received along the beam direction line 68 and the data used for the spectral Doppler display are acquired from echoes returning from the sample volume SV on the beam direction line. The Doppler flow direction cursor 66, used for angle correction, is aligned with the longitudinal orientation of the blood vessel 64 and is thus substantially parallel with the flow direction in the vessel, and the Doppler steering angle is the vertical angle of the color box 70 and the beam direction line 68, which are generally parallel to each other. In this example the Doppler steering angle is set to approximately a 60° angle with the longitudinal direction of the blood vessel 64.

Figure 3:
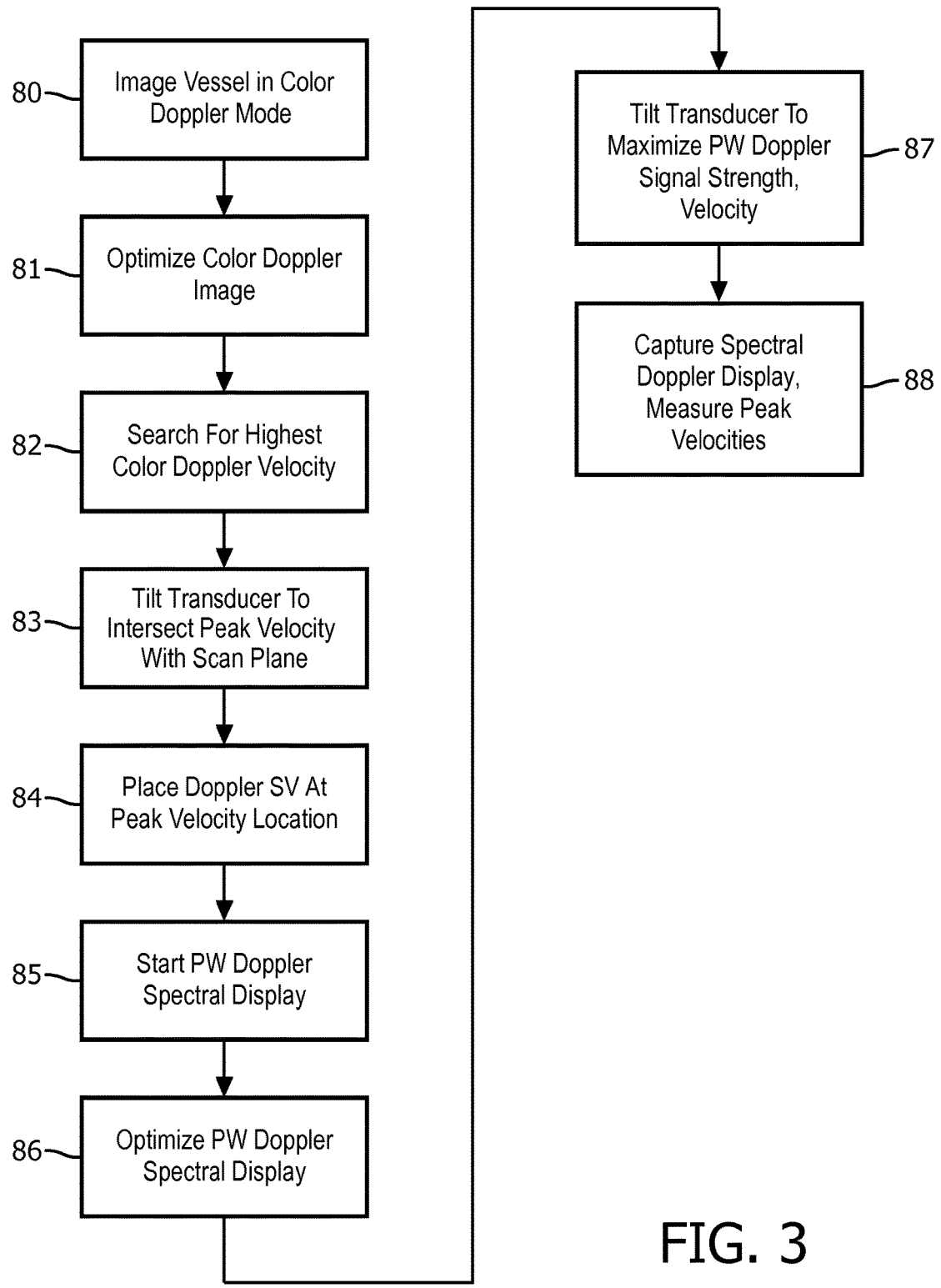
FIG. 3 illustrates the workflow of a typical ultrasound stenosis assessment exam.

With the aid of a duplex Doppler display as shown in FIG. 2, a typical ultrasound stenosis exam proceeds as shown by the workflow of FIG. 3. First, the ultrasound system is set to the color Doppler mode to image the site of the stenosis in a blood vessel 64 in a color Doppler image 60 as indicated at step 80. The color Doppler image is optimized in step 81 by positioning the sample volume SV over the vessel 64 and adjusting the color Doppler steering angle, the longitudinal angle of the color box 70. The clinician then examines the image to search for the highest velocity flow in the vessel 64 as represented by colors associated with the higher velocities on the color Doppler scale 61, in step 82. In step 83 the clinician tilts the probe 10 while continuing to observe the color Doppler image in an effort to ensure that the scan plane of the image intersects the vessel 64 at the location of the peak flow velocity. This is essentially a blind search because each change of the scan plane presents new Doppler values in a new image which must be examined carefully in comparison with colors previously seen in other planes to assure that the peak velocity color is present in the image. Once the clinician is confident she is imaging the peak velocity location, the PW (pulse wave) Doppler mode is activated to display the PW Doppler beam direction line 68 and the line is positioned and the Doppler sample volume SV placed on it at the peak velocity location in the image as indicated in step 84. Since a new image plane is being imaged, optimization of the color Doppler image (step 81) may have to be repeated. The scrolling display of the PW Doppler spectrum is now started (step 85), producing the spectral Doppler display 62 of flow velocities at the SV location as shown at the bottom of the screen. The PW Doppler display is optimized in step 86 by adjusting settings such as that for the Doppler scale, Doppler angle, sample volume size, and angle correction. The probe is now tilted again as indicated in step 87 to maximize the PW Doppler signal strength and/or velocity, to ensure that the maximum flow velocities are being recorded in the spectral display. The scrolling spectral Doppler display is captured (stopped on the screen; saved) in step 88, at which time the peak velocities and other parameters of the blood flow may be measured from the display.

Figure 4:
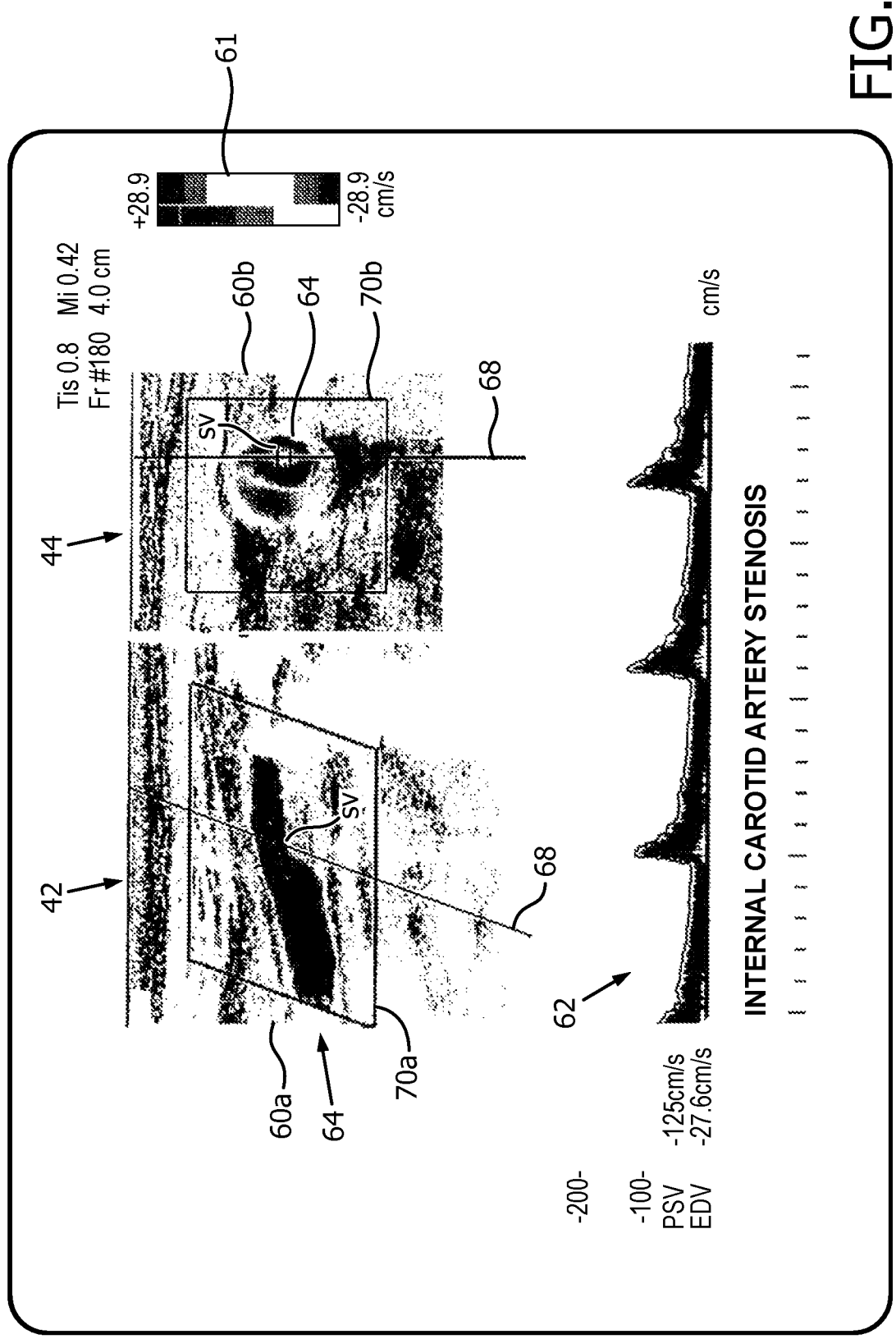
FIG. 4 illustrates an ultrasound display screen for an ultrasound stenosis assessment exam in accordance with the present invention.

As can be appreciated from the foregoing, this procedure entails a great deal of probe manipulation and ultrasound system setting adjustment, all of which benefit from extensive experience and expertise from the clinician. These difficulties are addressed in accordance with the present invention by conducting the stenosis exam with a matrix array probe operating in the biplane mode as illustrated by the ultrasound system screen display of FIG. 4 in conjunction with the workflow diagram of FIG. 5. FIG. 4 shows a duplex ultrasound display but with two biplane images 42 and 44. In the biplane mode a two dimensional array transducer 500 alternately scans two different planes in the body, producing the two images 42 and 44. Generally one of the images such as the left image in FIG. 4 is that of a reference plane projecting normal to the center of the transducer array. The second image, image 44 in this example, is then rotated and/or tilted about the plane of the reference image. In a preferred implementation of the present invention, both image planes can be repositioned with respect to each other. So that both left and right planes make sense and their orientation can be easily understood by the user, the planes preferably intersect at the location of the center of the SV and along a vector defined either by the PW Doppler beam line 68 or the color steering angle of color box 70 (if different). This means that, if the left image 42 is in the plane of the drawing, the right image plane 44 is tilted out of the plane of the drawing when Color/PW is steered in the left plane. Lateral movement by the user of the SV in the left plane will cause the right plane to translate laterally so that the right image 44 always shows where the SV is in that image plane. Moving the SV in the right plane 44 will likewise translate the plane of the left image, this time in elevation (in or out of the plane of the drawing). For a trapezoidal biplane format the planes (and the PW Doppler line 68) will originate from a common origin, and so all the planes will tilt instead of translate.

Figure 5:
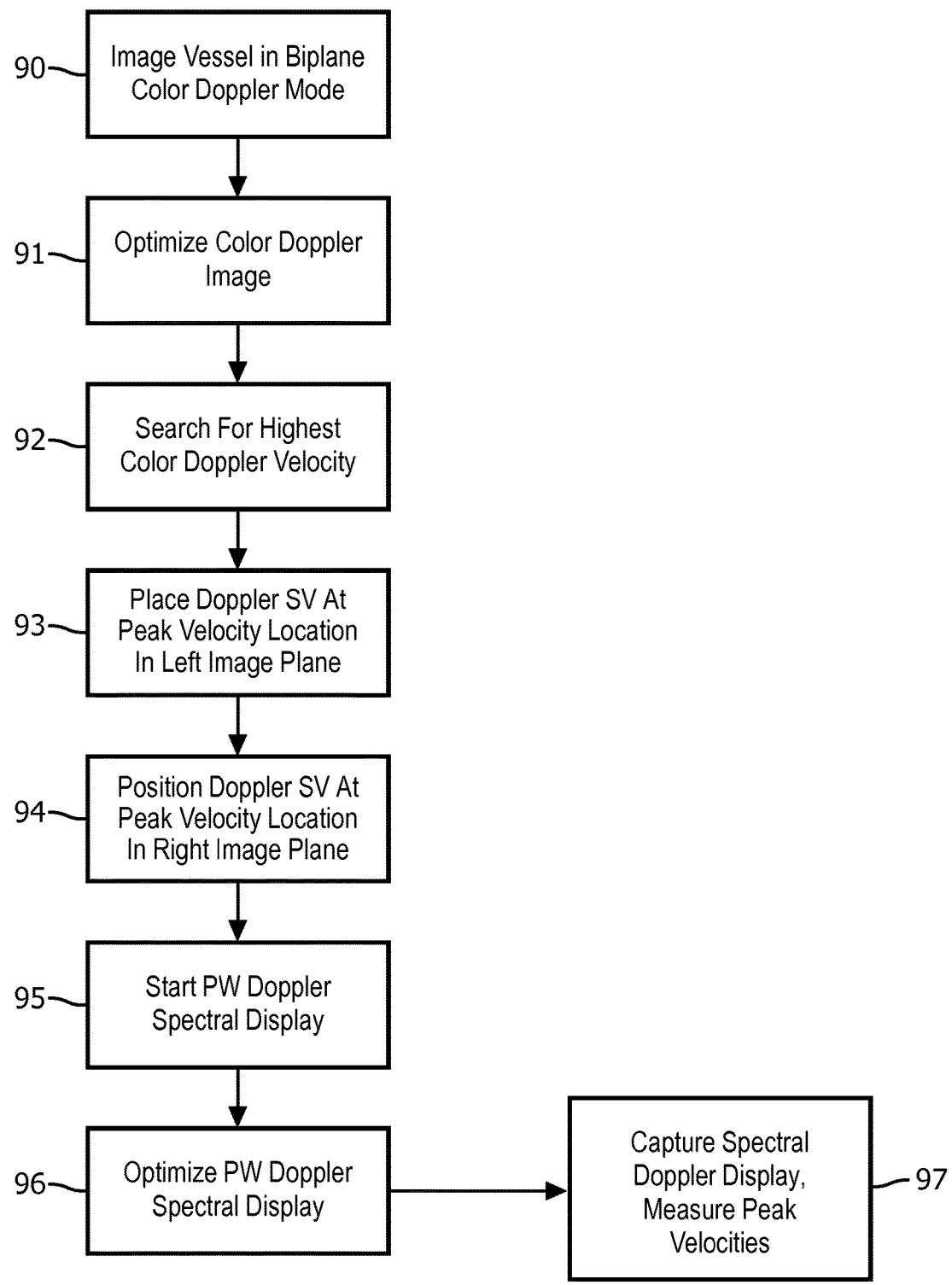
FIG. 5 illustrates the workflow of an ultrasound stenosis assessment exam in accordance with the principles of the present invention.

With the duplex display of FIG. 4, an ultrasound stenosis exam can proceed as shown by the workflow of FIG. 5. The stenotic blood vessel 64 is imaged in biplane in the color Doppler mode as indicated at step 90. In step 91 the color Doppler image is optimized by positioning the sample volume SV over the vessel 64 and selecting an optimal color Doppler steering angle, the angle of the color box 70a. The clinician examines the left biplane image 60a to search for the highest velocity flow in the vessel 64 as represented by colors associated with the higher velocities on the color Doppler scale 61, in step 92. In step 93 the PW Doppler mode is activated, the PW Doppler beam line 68 is displayed over the left image 60a, and the clinician adjust the positions of the line 68 and the sample volume SV along the line. In this example the plane of the right biplane image 60b is aligned with the PW Doppler beam line 68. In step 94 the SV shown in the right image 60b is adjusted to center it on the peak color velocity in the cross-sectional view of the vessel 64 in this image plane. The clinician can preferably adjust the position of the SV in the right image plane both laterally and axially onto the peak flow velocity in the right image. No color angle adjustment is needed for this image. When the SV is repositioned laterally, the left image plane may change slightly in elevation to keep both planes aligned along the PW beam line 68. In a simplified implementation the SV is restricted to only axial (depth) adjustment and lateral adjustment is done by moving or rocking the probe in elevation so that the line 68 is over the peak velocity location in the right image. Again, the left image plane plane may move in correspondence with the adjustment.

The scrolling of the PW Doppler spectral display 62 is started in step 95 and the spectral display is optimized as needed, as described above, in step 96. The scrolling spectral Doppler display is captured in step 97, and the peak velocities and other parameters of the blood flow measured from the display.

Figure 6:
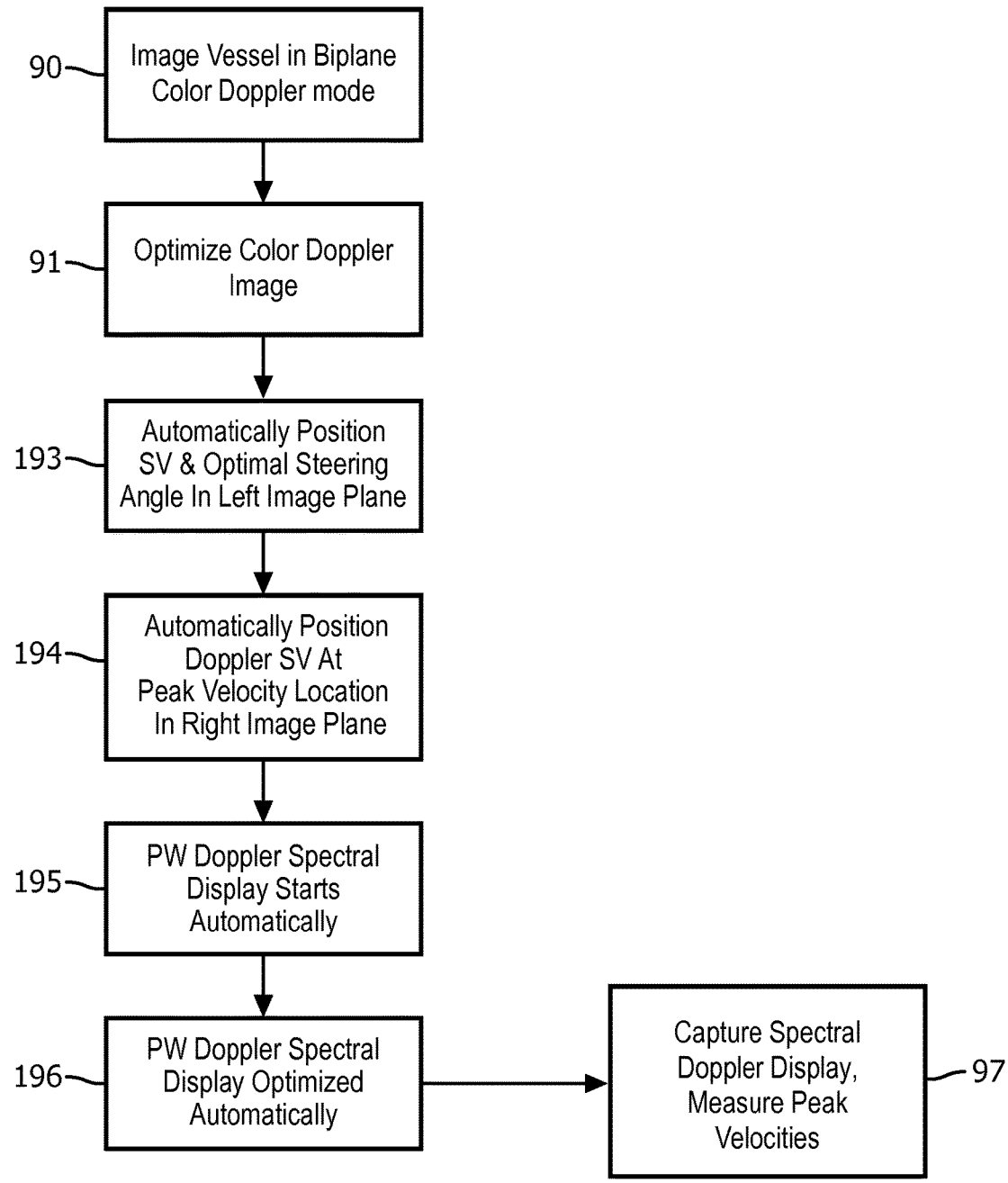
FIG. 6 illustrates the workflow of a highly automated ultrasound stenosis assessment exam in accordance with the principles of the present invention.

The procedure of the workflow of FIG. 5 can be automated to even further relieve user manipulation and increase precision as illustrated by the automated stenosis assessment workflow of FIG. 6, in which steps previously described in FIG. 5 are given the same reference numerals. In step 193 the positioning of the sample volume SV and the setting of the optimal Doppler steering angle in the left image plane are done automatically for the user. Apparatus and techniques for automating these adjustments are described in the aforementioned U.S. patent application Ser. No. 61/541,353, incorporated herein by reference. This application also describes the automatic setting of the angle correction cursor 66, as well as automated centering of the sample volume location in the color box 70a. The automated adjustment of the sample volume location in the left image plane 60a will cause a tilt or translation of the position of the plane of the right image 60b. In step 194 the processor 40 in a similar manner automatically positions the sample volume SV at the peak velocity location in the plane of the right image. Again, this will cause a translation or tilt effect on the left image plane. In step 195 the scrolling of the PW Doppler spectral display starts automatically after the previous adjustments are made, and in step 196 the spectral display is optimized automatically to set the Doppler scale, baseline, and gain as described in international patent publication WO 2003/019227 (Christopher et al.) entitled "AUTOMATIC OPTIMIZATION OF DOPPLER DISPLAY PARAMETERS." The clinician is thus quickly and accurately brought to the point where the Doppler spectrum of the stenotic blood flow can be captures and its characteristics measured.

While the method of the present invention is ideally suited for assessing the flow characteristics of a stenosis, it will be appreciated that the inventive method is useful in other cardiovascular procedures where the peak velocity of blood flow is to be measured, such as an investigation of the hemodynamics within the chambers of the heart and of blood flow through valves.

What is claimed is:

1. A method for operating an ultrasonic diagnostic imaging system having a matrix array probe operable in a biplane mode for the conduct of blood flow assessment, the method comprising:
   imaging a blood vessel in color Doppler mode in first and second image planes and simultaneously displaying first and second image displays, each associated with a respective one of the first and second image plane;
   locating a first peak velocity location in the first image plane;
   positioning a Doppler sample volume in the first image display to correspond with the first peak velocity location;
   displaying a Doppler beam line through the Doppler sample volume in the first image display;
   aligning the first and second image planes with the Doppler beam line;
   centering the Doppler sample volume at a second peak velocity location in the second image plane;
   generating a spectral Doppler display of flow data for flow velocities at the location of the Doppler sample volume; and
   measuring velocity characteristics using the flow data of the acquired spectral Doppler display.

2. The method of claim 1, wherein the imaging in the first and second image planes comprises alternately scanning the first and second image planes.

3. The method of claim 1, wherein the imaging in the first and second planes comprises scanning an image plane intersecting the first image plane along the Doppler beam line for imaging in the second image plane.

4. The method of claim 3, further comprising repositioning a Doppler sample volume graphic along the Doppler beam line in the first image display to correspond with the second peak velocity location in the second image plane.

5. The method of claim 1, wherein centering the Doppler sample volume at the second peak velocity location in the second image comprises positioning a Doppler sample volume graphic in the second image display at the second peak velocity location in the second image plane responsive to user input.

6. The method of claim 1, wherein generating a spectral Doppler display further comprises acquiring a Doppler spectral display by means of PW Doppler acquisition.

7. The method of claim 3, wherein generating a spectral Doppler display further comprises acquiring a Doppler spectral display by means of PW Doppler acquisition in the direction of the Doppler beam line.

8. The method of claim 1, further comprising automatically repositioning the first image plane to include the second peak velocity location in the second image plane.

9. The method of claim 1, wherein centering the Doppler sample volume at the second peak velocity location in the second image plane is responsive to user input.

10. The method of claim 1, wherein at least one of positioning the Doppler sample volume in the first image display to correspond with the first peak velocity location and centering the Doppler sample volume at the second peak velocity location in the second image plane further comprises automatically positioning a sample volume graphic in the respective image display.

11. The method of claim 1, wherein the spectral Doppler display is a scrolling spectral Doppler display.

12. The method of claim 1, wherein imaging a blood vessel in color Doppler mode further comprises automatically optimizing a biplane color Doppler image by positioning the Doppler sample volume over the blood vessel and selecting an optimal Doppler steering angle.

13. The method of claim 1, wherein generating a spectral Doppler display further comprises automatically optimizing a spectral Doppler display.

14. The method of claim 1, wherein imaging a blood vessel in color Doppler mode further comprises imaging the blood vessel in the first image plane in a longitudinal cross-sectional view and imaging the blood vessel in the second image plane in a transverse cross-sectional view.

* * * * *